US008598815B2

(12) United States Patent
Glaister et al.

(10) Patent No.: US 8,598,815 B2
(45) Date of Patent: Dec. 3, 2013

(54) CONTROLLABLE TRANSVERSE ROTATION ADAPTOR

(75) Inventors: Brian Glaister, Seattle, WA (US); Glenn Klute, Seattle, WA (US)

(73) Assignee: University of Washington Through Its Center for Commercialization, Seattle, WA (US)

( * ) Notice: Subject to any disclaimer, the term of this patent is extended or adjusted under 35 U.S.C. 154(b) by 0 days.

(21) Appl. No.: 13/380,487

(22) PCT Filed: Jun. 21, 2010

(86) PCT No.: PCT/US2010/039356
§ 371 (c)(1), (2), (4) Date: Feb. 29, 2012

(87) PCT Pub. No.: WO2011/005482
PCT Pub. Date: Jan. 13, 2011

(65) Prior Publication Data
US 2012/0153875 A1     Jun. 21, 2012

Related U.S. Application Data

(60) Provisional application No. 61/219,271, filed on Jun. 22, 2009.

(51) Int. Cl.
*B60K 6/36* (2007.10)
*H02K 7/10* (2006.01)

(52) U.S. Cl.
USPC .......... 318/9; 318/139; 318/400.05; 318/434; 623/24; 623/27; 623/32; 623/46

(58) Field of Classification Search
USPC ............ 318/9, 139, 400.15, 434; 623/24, 27, 623/32, 46
See application file for complete search history.

(56) References Cited

U.S. PATENT DOCUMENTS

| | | | |
|---|---|---|---|
| 4,512,766 A | 4/1985 | Vailancourt | |
| 6,086,607 A | 7/2000 | Cragg et al. | |
| 6,517,585 B1 * | 2/2003 | Zahedi et al. | 623/24 |
| 7,044,937 B1 | 5/2006 | Kirwan et al. | |
| 2004/0068325 A1 * | 4/2004 | Phillips et al. | 623/35 |
| 2006/0207959 A1 | 9/2006 | Woolston | |

(Continued)

OTHER PUBLICATIONS

International Search Report and Written Opinion mailed Mar. 4, 2011 in PCT Application No. PCT/US2010/039356 filed Jun. 21, 2010.

*Primary Examiner* — Erick Glass
(74) *Attorney, Agent, or Firm* — Kilpatrick Townsend and Stockton LLP

(57) ABSTRACT

Torsional loads can impart painful and potentially injurious shear stresses upon residual limb soft tissues in lower limb amputees. To protect the soft tissues, a controllable transverse rotation adapter (TRA) has been developed that permits rotation of the prosthetic socket relative to the prosthetic foot, relieving some of the rotational loads experienced by the residual limb, and controlling either the stiffness resisting the transverse rotational torque, or the torque. This TRA uses series elastic actuator (SEA) technology and includes a prime mover, a speed reduction device, and a torsion spring mounted in series. By measuring a displacement of the spring (e.g., using a strain gauge), motor current, and the motor shaft position, the load torque and position can be used to calculate actual stiffness or applied torque. The motor position is then adjusted relative to the load, to control the effective stiffness or torque.

23 Claims, 12 Drawing Sheets

(56) References Cited

U.S. PATENT DOCUMENTS

| | | | |
|---|---|---|---|
| 2007/0043449 A1* | 2/2007 | Herr et al. | 623/24 |
| 2007/0162152 A1* | 7/2007 | Herr et al. | 623/24 |
| 2008/0033579 A1* | 2/2008 | Phillips et al. | 623/53 |
| 2008/0300692 A1* | 12/2008 | Moser et al. | 623/55 |
| 2009/0265018 A1* | 10/2009 | Goldfarb et al. | 623/40 |
| 2011/0257764 A1* | 10/2011 | Herr et al. | 623/24 |

* cited by examiner

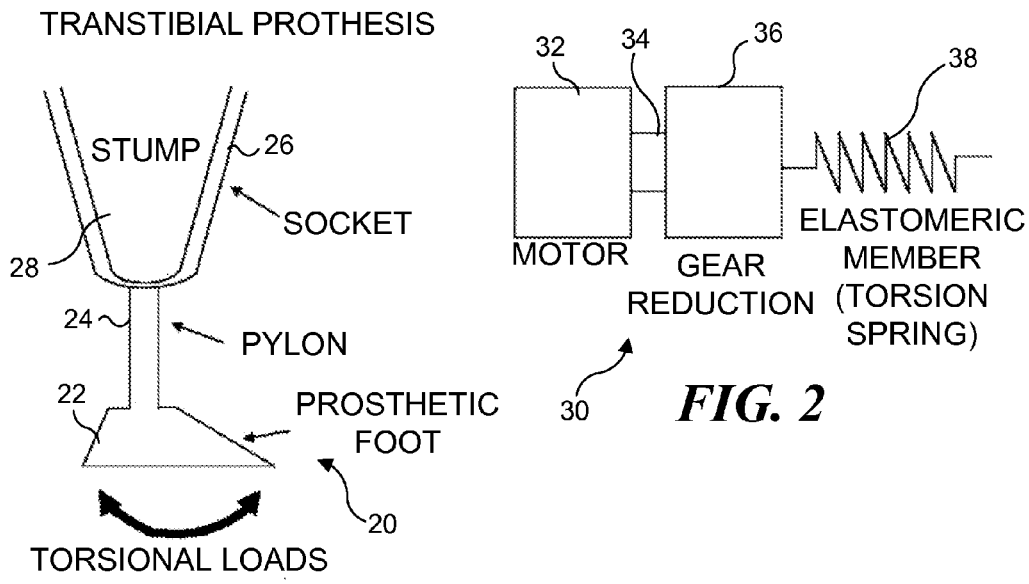
FIG. 1 (PRIOR ART)
FIG. 2
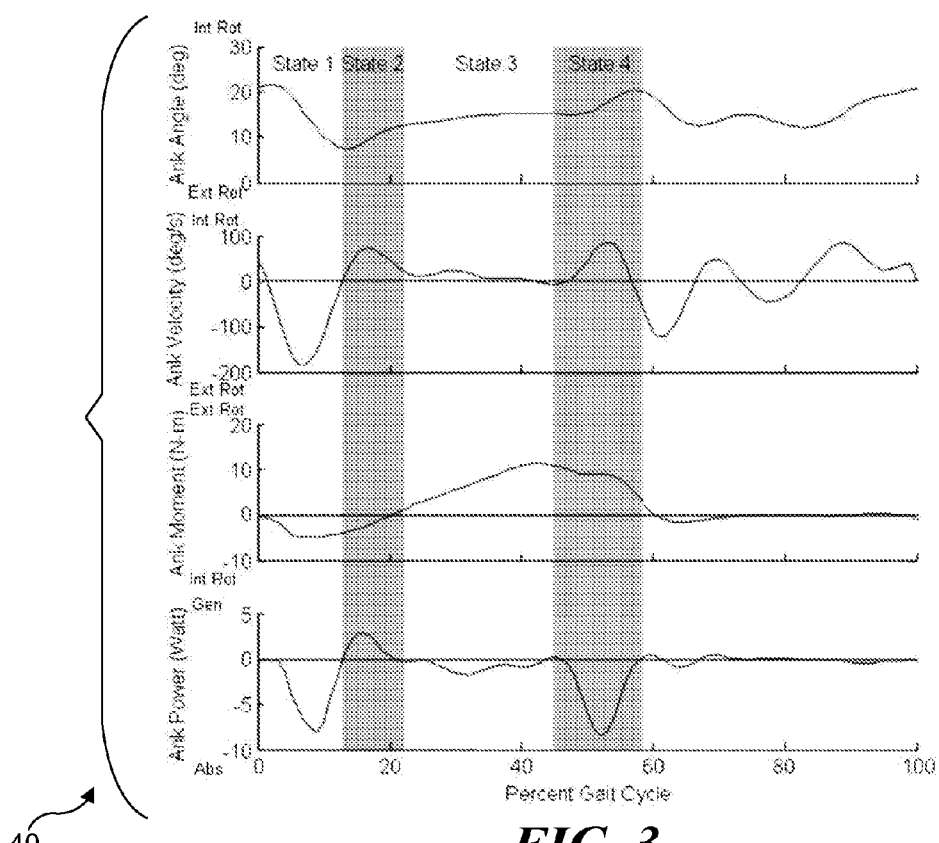
FIG. 3

CONTROLLABLE TRANSVERSE ROTATION ADAPTOR

CROSS REFERENCES TO RELATED APPLICATIONS

The present application is a U.S. National Phase Application under 35 U.S.C. §371 of International Application No. PCT/US2010/039356, filed on Jun. 21, 2010, which claims priority to U.S. Provisional Patent Application No. 61/219,271, filed Jun. 22, 2009, the benefit of the filing date of which is hereby claimed under 35 U.S.C. §119(e) and each of which are incorporated herein in their entirety by reference.

STATEMENT AS TO RIGHTS TO INVENTIONS MADE UNDER FEDERALLY SPONSORED RESEARCH OR DEVELOPMENT

This invention was made with U.S. government support under A36111 awarded by Veterans Administration Puget Sound Healthcare System. The government has certain rights in the invention.

BACKGROUND

Turning is a ubiquitous task for human ambulation, and this task has been shown to be related to falling and fall-related injuries in Parkinson's Disease patients and for the elderly, and likely creates difficulties for lower limb amputees as well. Unlike an intact leg, which transfers loads to the skeletal system via fatty pads on the bottom of the foot, in amputees, as shown in a schematic diagram 20 in FIG. 1, loads are transferred from the ground to a prosthetic socket 26 via a prosthetic foot 22 and a rigid aluminum tube called a pylon 24. The prosthetic socket then transfers the loads to the soft tissues of a stump 28, or residual limb. When performing turning maneuvers, amputees experience increased transverse plane torques. These increased transverse plane torques result in increased shear stresses that are believed to be associated with pain, and the formation of epidermoid cysts and ulcers, which can require several visits to a physician to manage. Thus, new technology is needed to improve comfort and prevent injury related to transverse plane torques during amputee turning gait.

The intact human ankle can serve as inspiration for a prosthetic device to reduce torsional loads while turning, since the actual ankle permits limited motion in the transverse plane. Previous research has investigated transverse plane ankle behavior and found that it behaves as a passive system with variable stiffness, both throughout the gait cycle and between straight and different turning steps. Despite this behavior, previous attempts to reduce transverse plane loading have focused on technologies with fixed stiffness.

To protect the soft tissues from the effects of torsional loads, which can impart painful and potentially injurious shear stresses upon residual limb soft tissues in lower limb amputees, prosthetic manufacturers have developed transverse rotation adapters (TRAs) that are essentially torsional springs mounted in the pylon of the prosthesis, which permit the prosthetic socket to rotate relative to the prosthetic foot, relieving some of the load acting on the residual limb. A variety of stiffness values are available for TRAs, allowing prosthetists to choose linear and nonlinear options and even allowing different values to be chosen for external and internal rotation. But once installed in the TRA, the stiffness does not vary as it does in the human ankle While it would be advantageous to be able to adjust the stiffness of the torsional spring to suit different activities, once installed, the stiffness of conventional TRAs cannot be easily adjusted. Any adjustment requires removal of the prosthesis and either replacement of the torsion spring or adjustment of the spring force provided by the torsion spring.

Another passive strategy that has been employed to reduce transverse loading is embodied in the Rotasafe™ device. This device is essentially a slip-clutch designed to prevent over-rotation of osseointegrated implants. Slip-clutches use static friction to maintain torsional rigidity until a certain torque is reached, at which point, the slip-clutch allows rotation, which, in the case of the Rotosafe™, acts to prevent damage to the bone-implant interface. Effectively, this device enables a binary variation selection between stiffness values (mainly, one very stiff and one soft), but cannot replicate the multitude and range of elastic behaviors exhibited by the human ankle. Furthermore, while the device can save an implant from excessive torques, the slipping rotations might induce falls that can cause other injuries.

In addition to preserving residual limb health, another important challenge for lower limb prosthetic design is to improve the metabolic cost of walking for amputees. Walking with a prosthesis requires much more metabolic energy to walk than is expended by a person with intact limbs. Indeed, dysvascular transfemoral amputees require more than twice as much oxygen to walk a meter than intact individuals. Other amputee levels and etiology also require considerably more oxygen to walk than intact individuals.

The cause of the elevated metabolic cost associated with amputee gait is largely unknown, and most of the research in the area has focused on how different prosthetic components affect metabolic cost. Prosthetic feet are some of the more popular components studied. With the advent of flexible energy storage and release feet, a number of researchers have investigated whether these feet can reduce the metabolic cost of walking Unfortunately, only three of the studies (of nine total) were able to detect differences in metabolic cost. Furthermore, one of those studies detected differences only for higher walking speeds, and the differences in the other studies were so small as to lack clinical significance, despite their statistical significance. Thus, it appears that energy storage and release feet have had limited success in reducing the metabolic cost of walking for amputees.

With the advent of microprocessor-controlled prosthetic knees, researchers again raised the question of whether prosthetic technology could reduce the metabolic cost of walking and again had mixed results. One group of researchers compared the C-Leg to the Mauch SNS prosthetic knee with eighteen transfemoral amputees and was unable to detect a difference in metabolic cost. Others compared the C-Leg, Rheo, and Mauch SNS knees and found that amputees had 3% and 5% lower metabolic rates with the C-Leg and Rheo knees, respectively, than with the Mauch SNS. Still another research group found that the C-Leg reduced the metabolic cost by 6% compared to a mechanical knee. Accordingly, while some studies were able to detect a metabolic benefit of using microprocessor-controlled prosthetic knees, these benefits were small compared to the enormous metabolic losses associated with transfemoral amputee gait. Furthermore, it should be noted that the two studies that detected metabolic benefits were funded by manufacturers of microprocessor-controlled knees, while the study that did not detect a benefit was funded by the U.S. government.

While innovations in energy storage and release feet and microprocessor-controlled knees have been unable to meaningfully decrease the metabolic cost of walking for lower limb amputees, recent research with inverted pendulum models of gait may hint at more fruitful interventions. Historically, walking has been believed to employ six kinematic features of gait to reduce the vertical displacement of the body center of mass (COM) in order to minimize metabolic cost. The inverted pendulum theory of gait proposes instead that the stance limb behaves like an inverted pendulum and that there are metabolic benefits associated with exploiting this natural dynamic behavior. With the inverted pendulum theory, step-to-step transitions are major sources of metabolic cost. More specifically, in order to redirect the COM along another pendular arc at the end of a step, the leading and trailing limbs perform negative and positive work simultaneously which exerts a metabolic cost. It has been found that transtibial amputees have difficulty generating positive work when the prosthetic leg trails, suggesting that a powered prosthetic ankle might decrease the step to step transitions and, consequently, the metabolic cost. Indeed, preliminary results with a powered sagittal ankle system have been able to reduce metabolic cost by an average of 14% with three subjects. In addition to the sagittal plane, considerable work must be performed to redirect the COM in the frontal plane, as well, suggesting that more metabolic gains can be achieved with active technology to propel the COM in this plane.

Accordingly, a new generation of technology is needed that enables the transverse loading to be varied across a wide range of stiffness values and/or torque values. It would also be desirable to employ an active approach to control the effective stiffness of rotation in a prosthesis, to be more responsive to loading changes. It would also be desirable to enable the stiffness of the loading to be readily varied with a control to enable an amputee to more effectively engage in various activities that benefit from the application of different levels of torsional stiffness. As a further benefit, the use of such a prosthesis should substantially reduce the metabolic cost to the subject by providing a gait that more closely replicates that of an intact individual.

SUMMARY

In order to allow lower limb amputees to adjust torsional stiffness, an exemplary controllable TRA has been developed. This adaptor uses a series elastic actuator (SEA) technology and includes a prime mover, such as an electric motor or other type of actuator, a gear reduction assembly, and a spring of known stiffness—all mounted in series along a longitudinal axis of the TRA. After measuring the displacement of the spring, the spring torque can be calculated. Then, by adjusting the prime mover position relative to the load, the effective stiffness of the adaptor can be controlled.

Accordingly, an SEA and impedance control system has been developed to be used in a prosthetic limb. With a prosthesis that includes this novel TRA, amputees can set the impedance control system input to a desired effective stiffness or can choose a torque setting that is suitable for different activities. For example, an amputee might want a very stiff TRA in a prosthesis to maximize its performance during high intensity activities like playing tennis, but then desire a soft TRA in the prosthesis to maximize comfort during everyday activities, like walking. Control of torque might be better during high intensity activities, to minimize the metabolic effort on the user, while during daily activities of longer duration and lower intensity, the user may want to control the TRA to achieve the desired stiffness. With this new TRA, amputees can adjust the TRA stiffness or torque in a prosthesis simply by turning a dial or similarly providing a control input change.

To design the control system, two levels of control were considered for an exemplary embodiment. The lowest level control system controls the effective stiffness or torque of the prosthesis through an impedance or moment control strategy, respectively. The next level control loop above the impedance system supplies a desired stiffness or torque at different periods of the gait cycle through a finite state strategy.

An actuator for an exemplary TRA that implements this functionality comprises a compact actuator, such as a direct current (DC) motor (with brushes), and a lightweight harmonic drive transmission (or other type of gear reduction mechanism), used with a torsion spring or other type of elastic element. The appropriate stiffness for the elastic element used with the TRA can be chosen by comparing the effect of stiffness on motor power, spring power amplification, and control stability through simulation experiments. Once the stiffness is chosen, the appropriate physical elastic element can be designed and fabricated. A housing for the adaptor integrates the actuator and torsion spring into a prosthesis that can be worn on a residual lower limb.

This application specifically incorporates herein by reference, the disclosure and drawings of the provisional patent application identified above as a related application.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1 (Prior Art) is a schematic diagram that illustrates an exemplary conventional transtibial prosthesis;

FIG. 2 is a schematic diagram illustrating an exemplary series elastic actuator (SEA);

Figure 4:
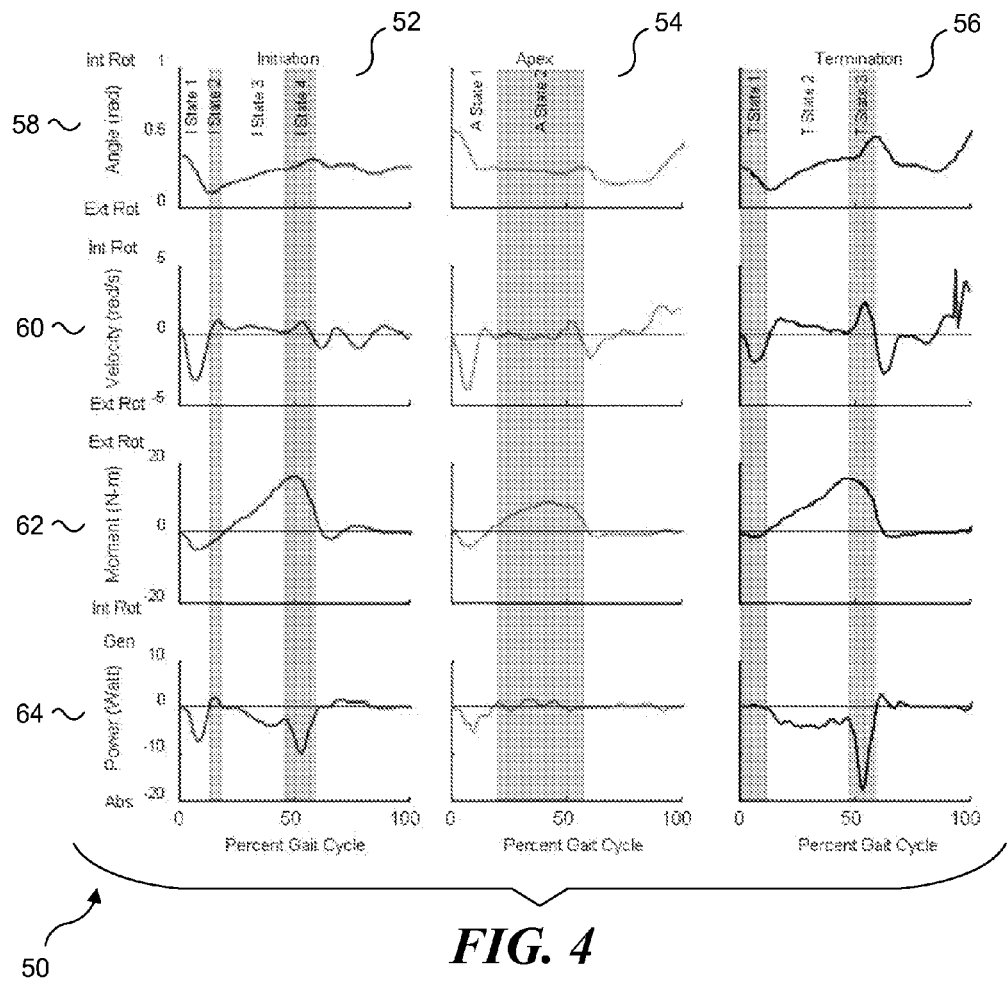
Figure 5:
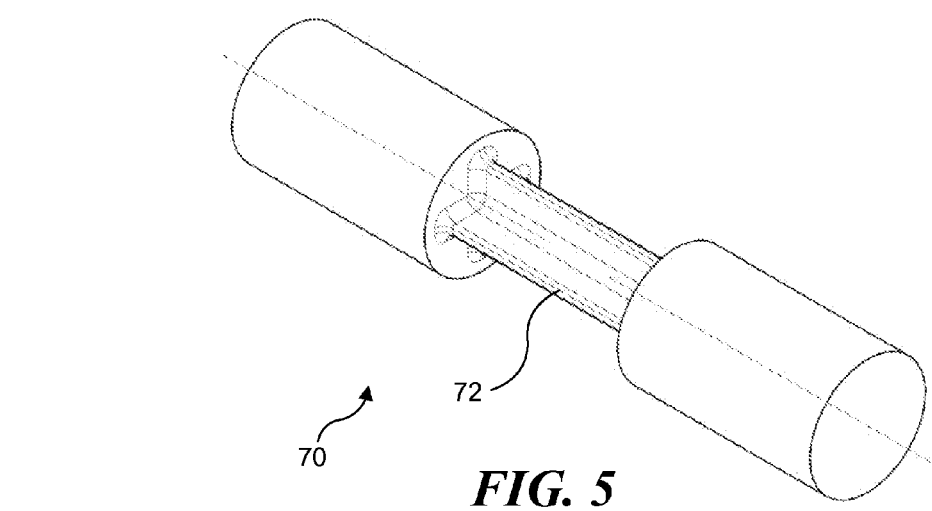
Figure 6:
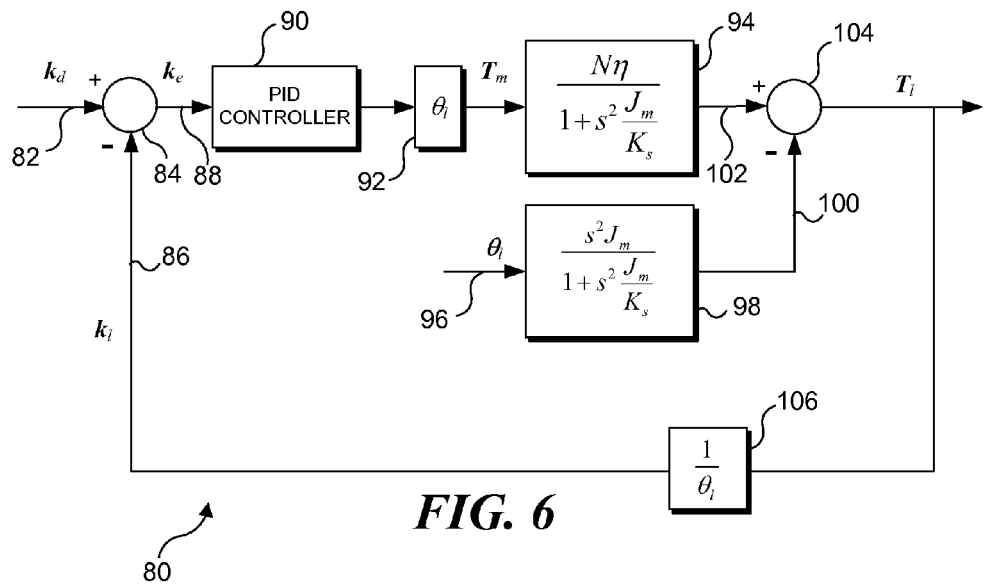
Figure 7:
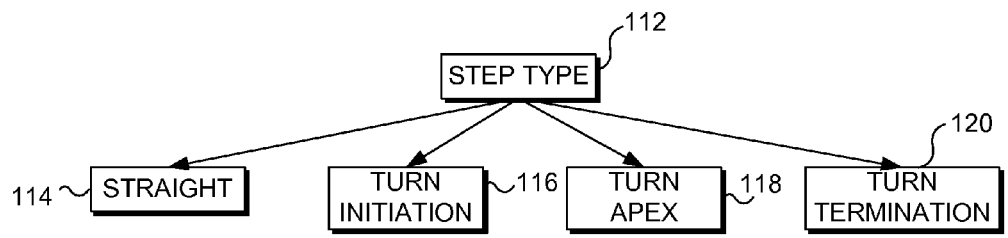
Figure 12:
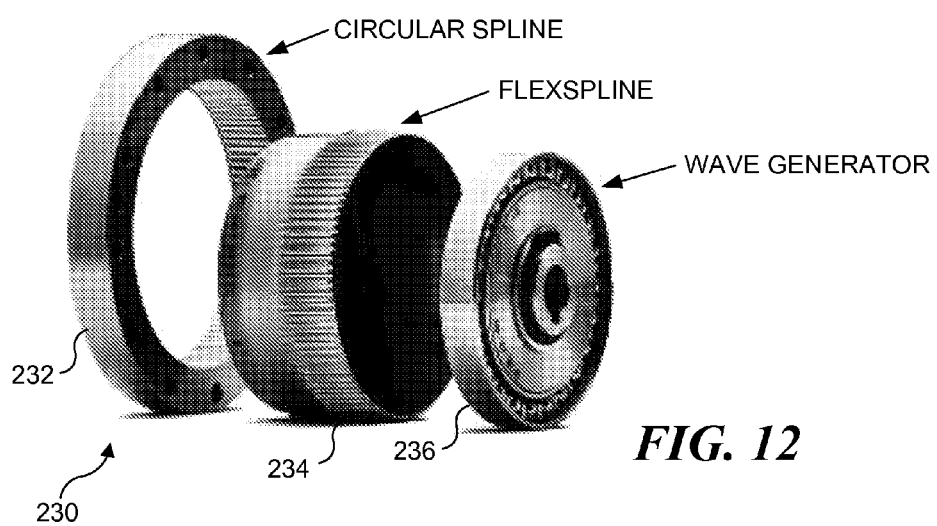
Figure 8:
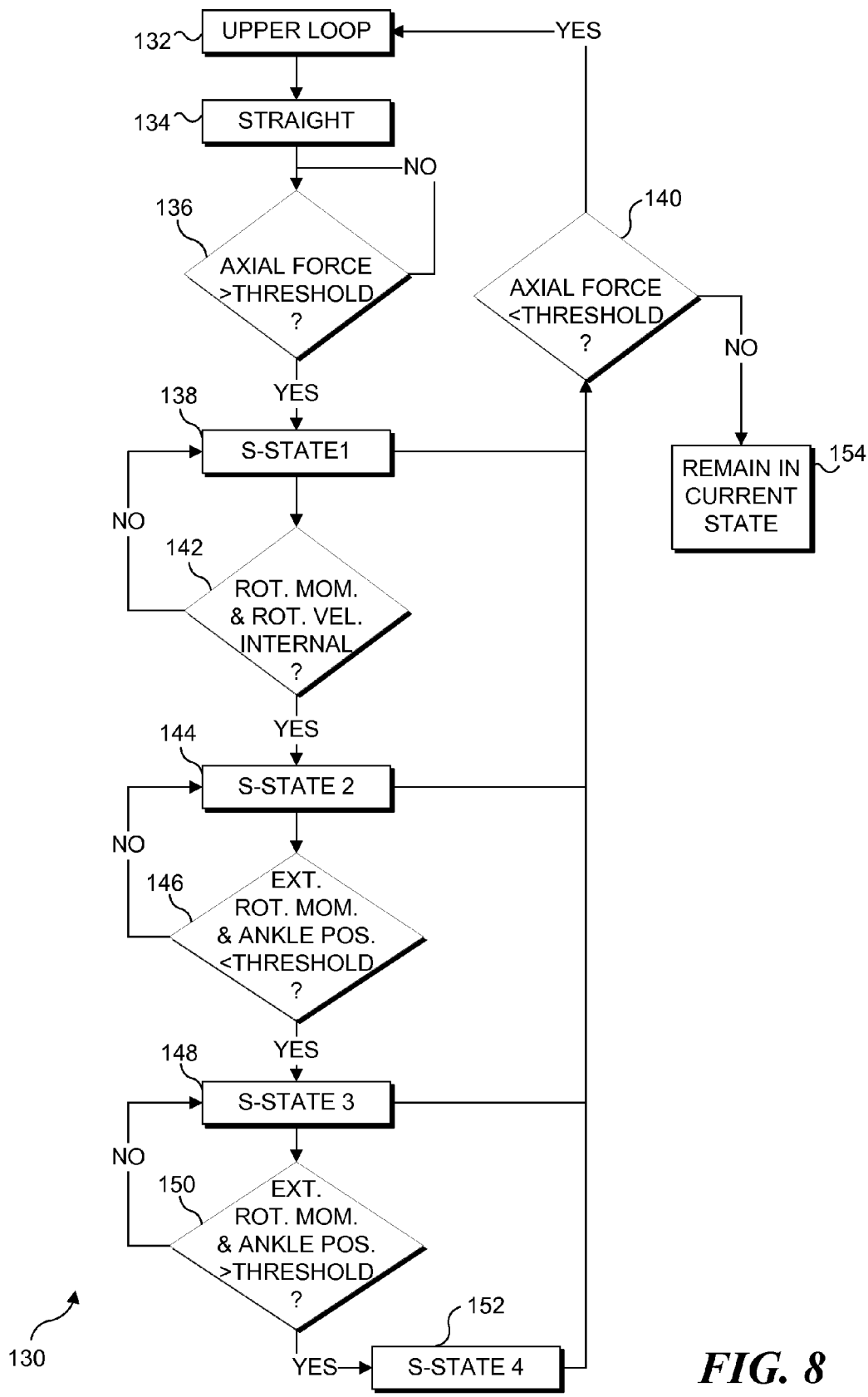
Figure 9:
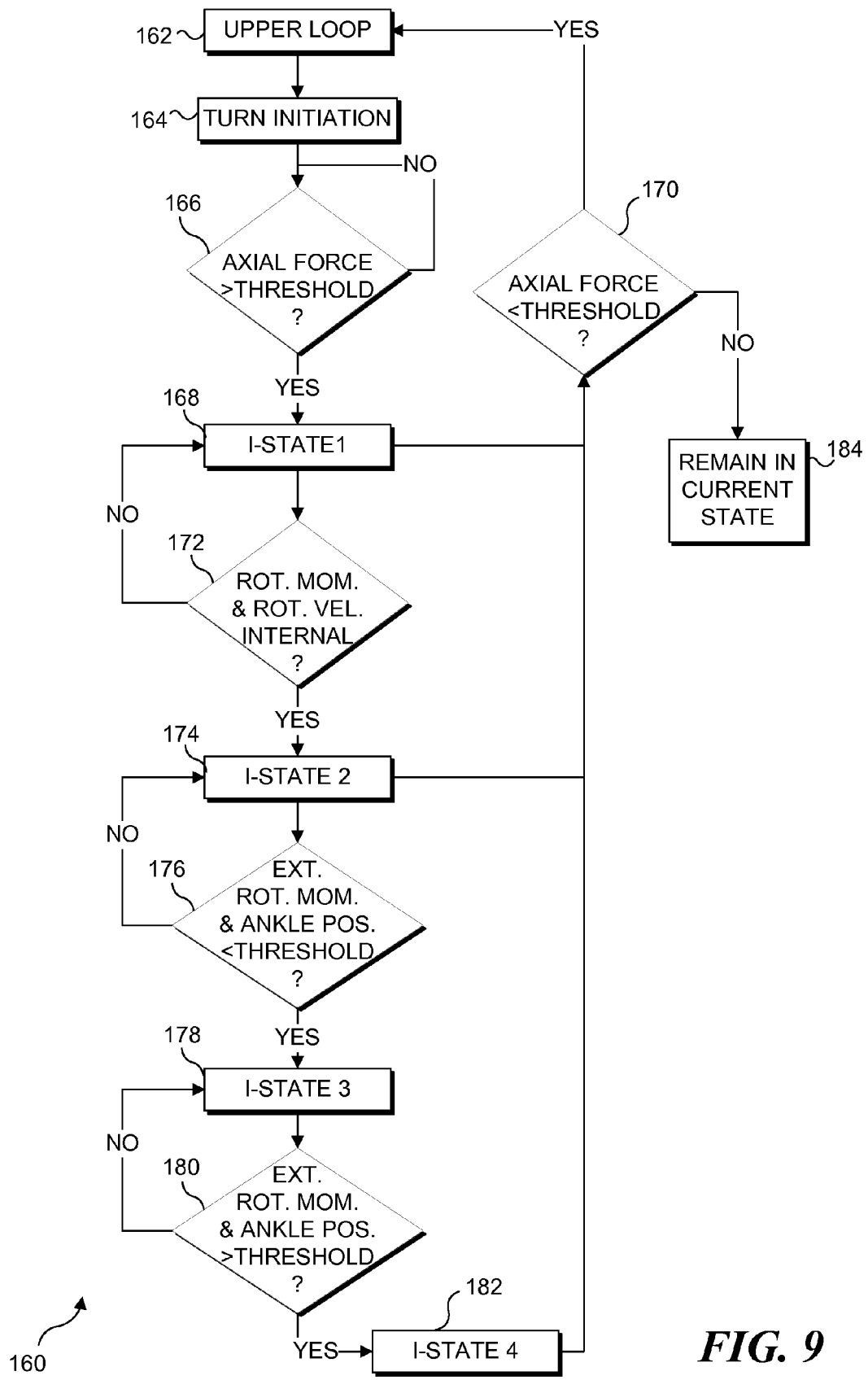
Figure 10:
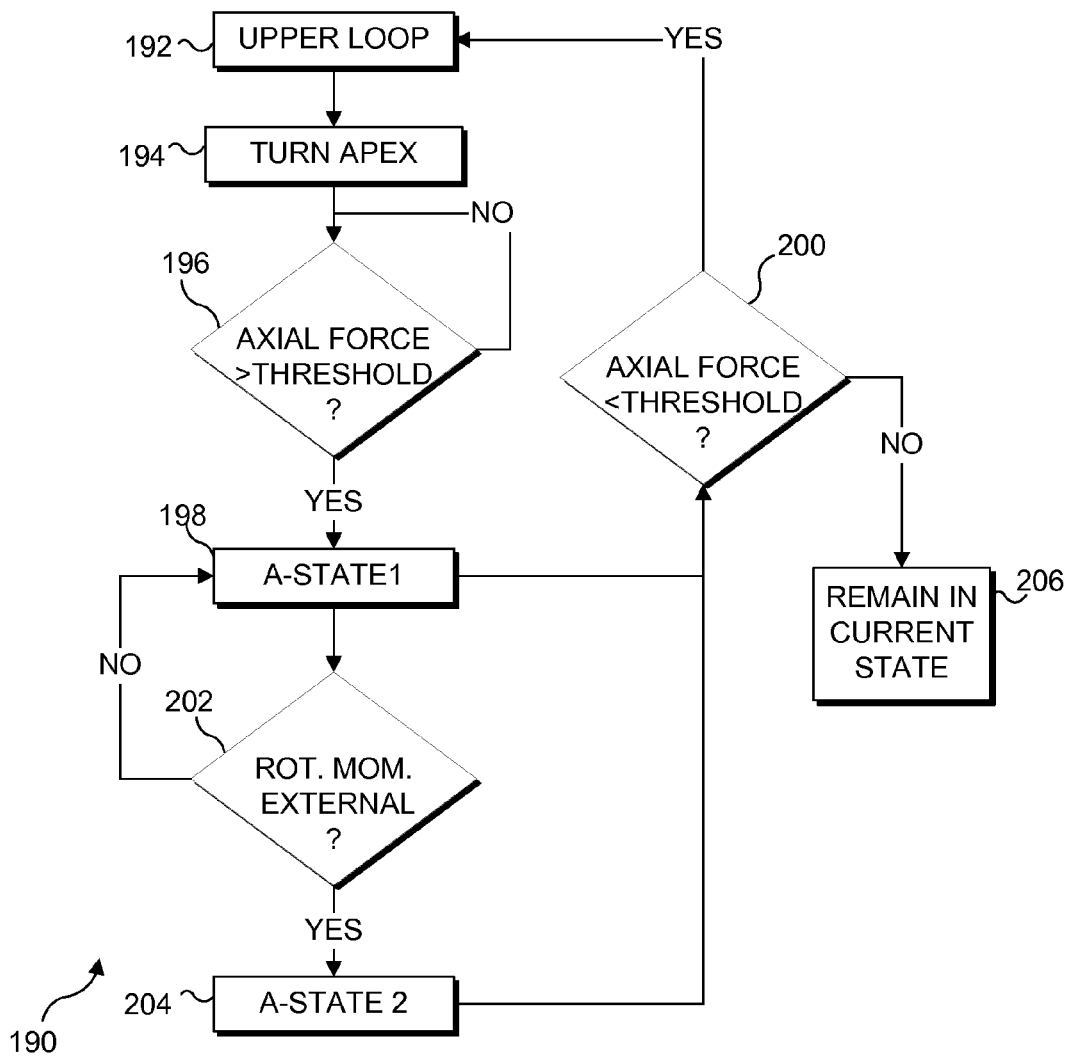
Figure 11:
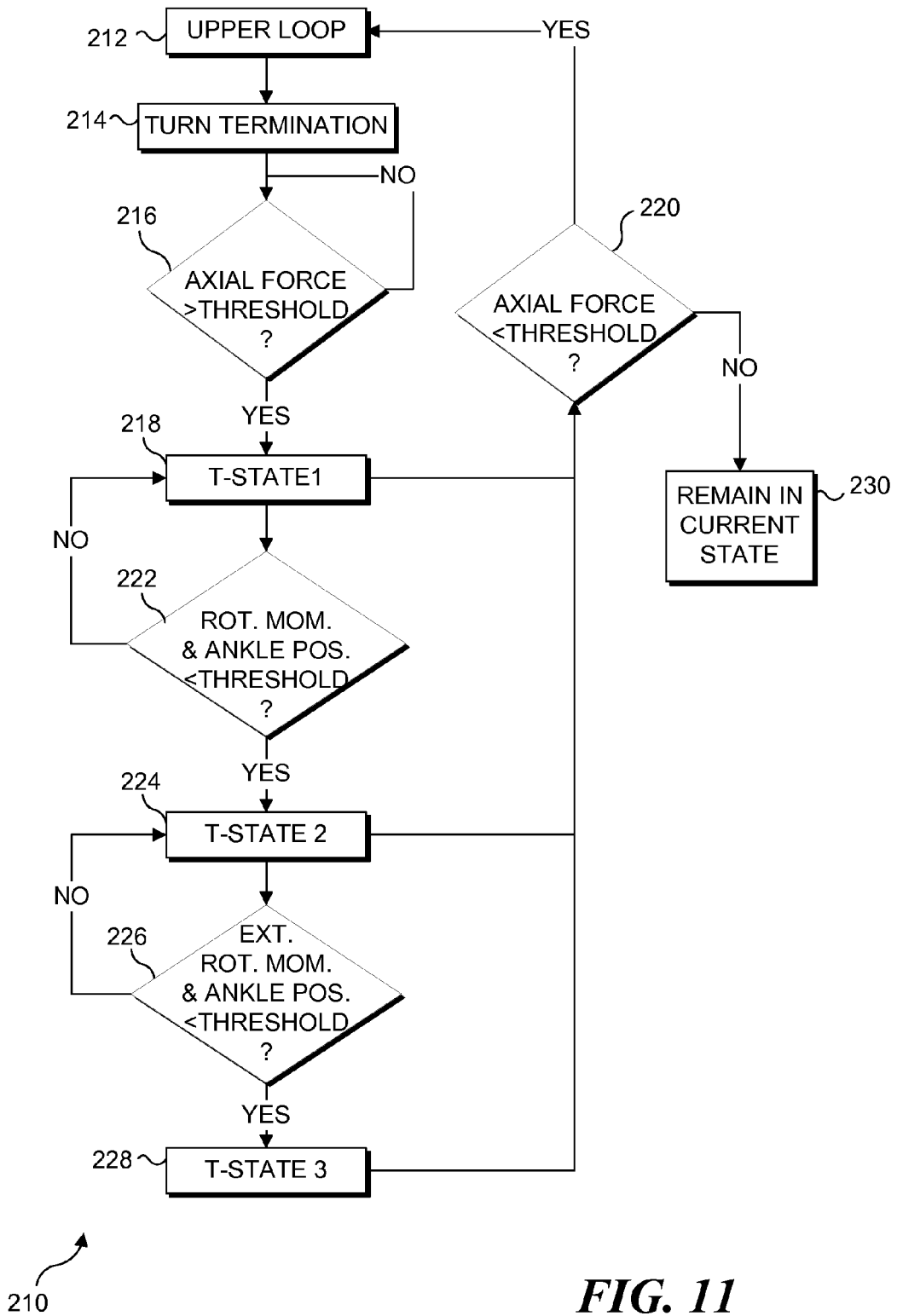
Figure 13:
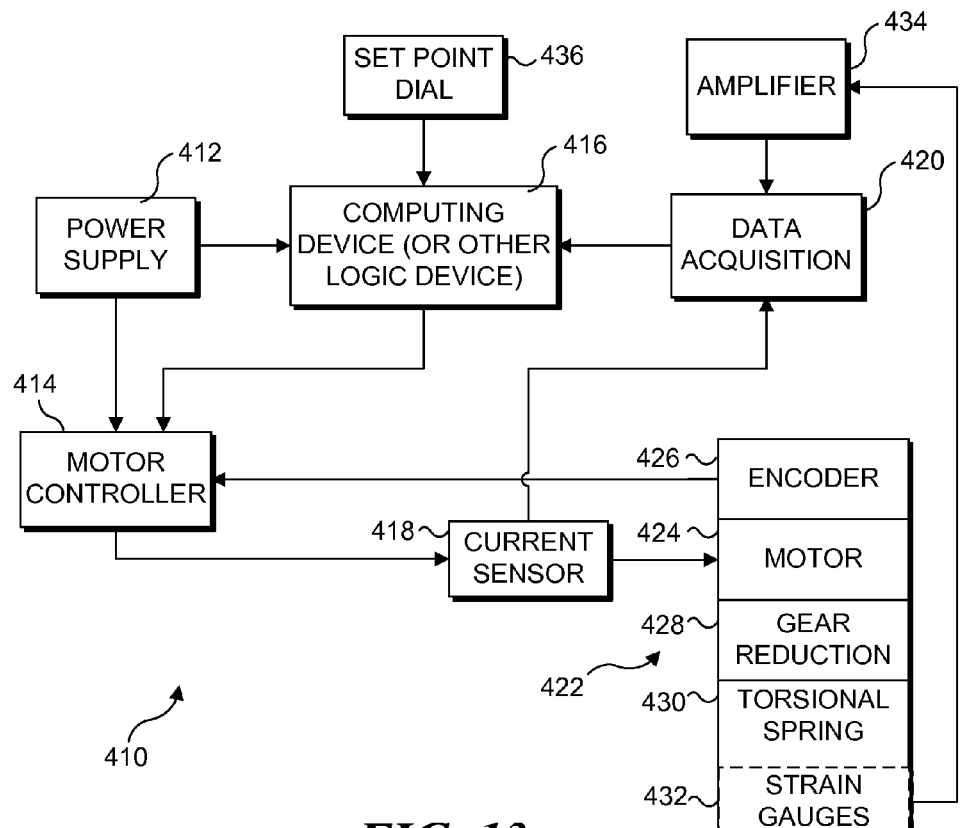
Figure 14:
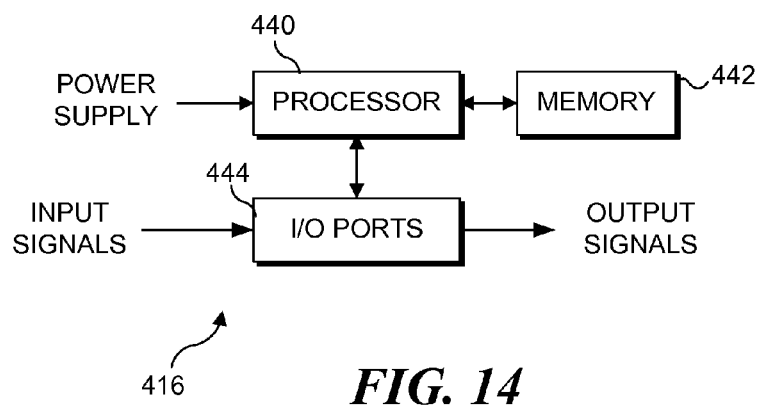
Figure 15:
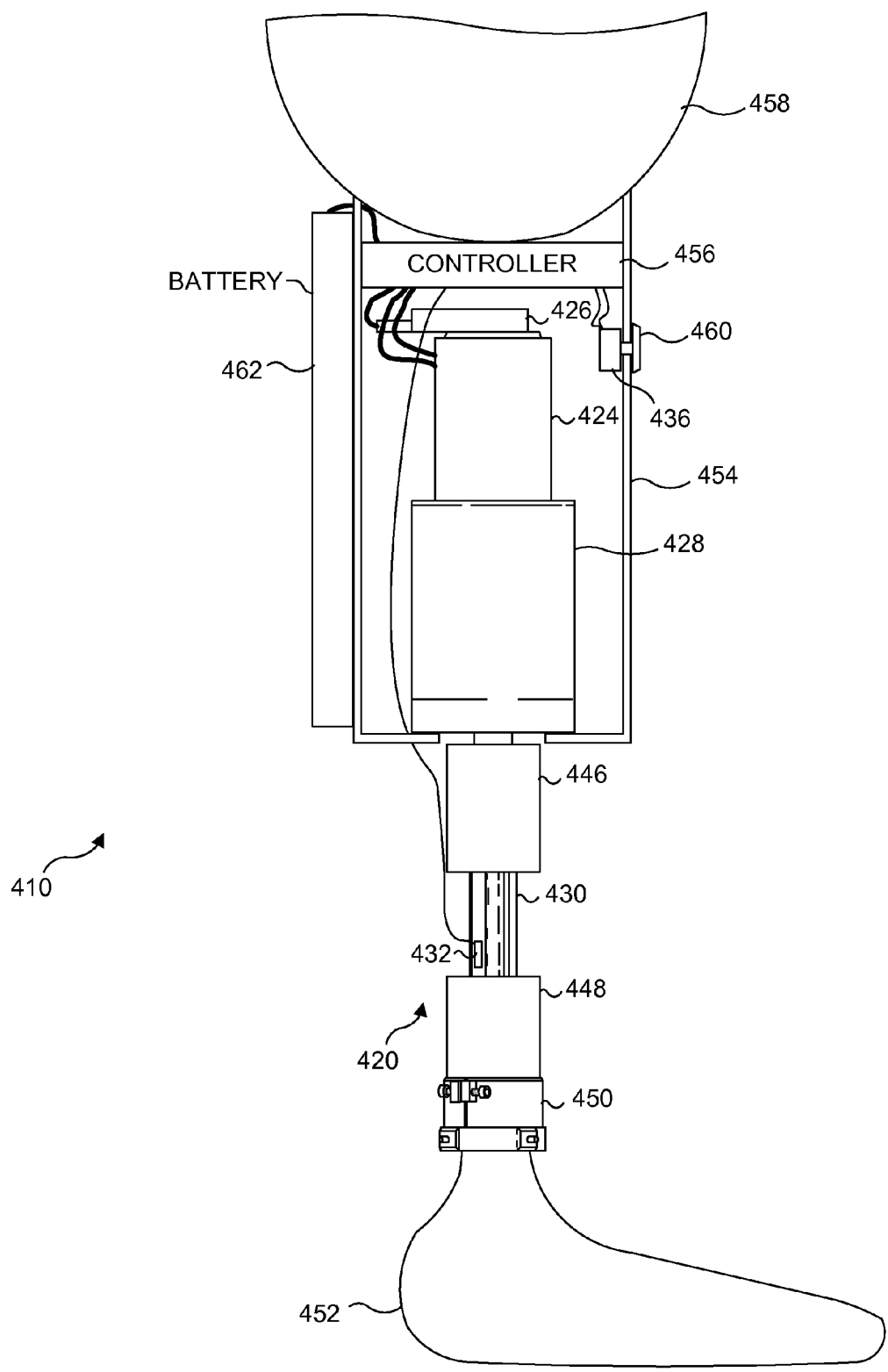
Figure 16:
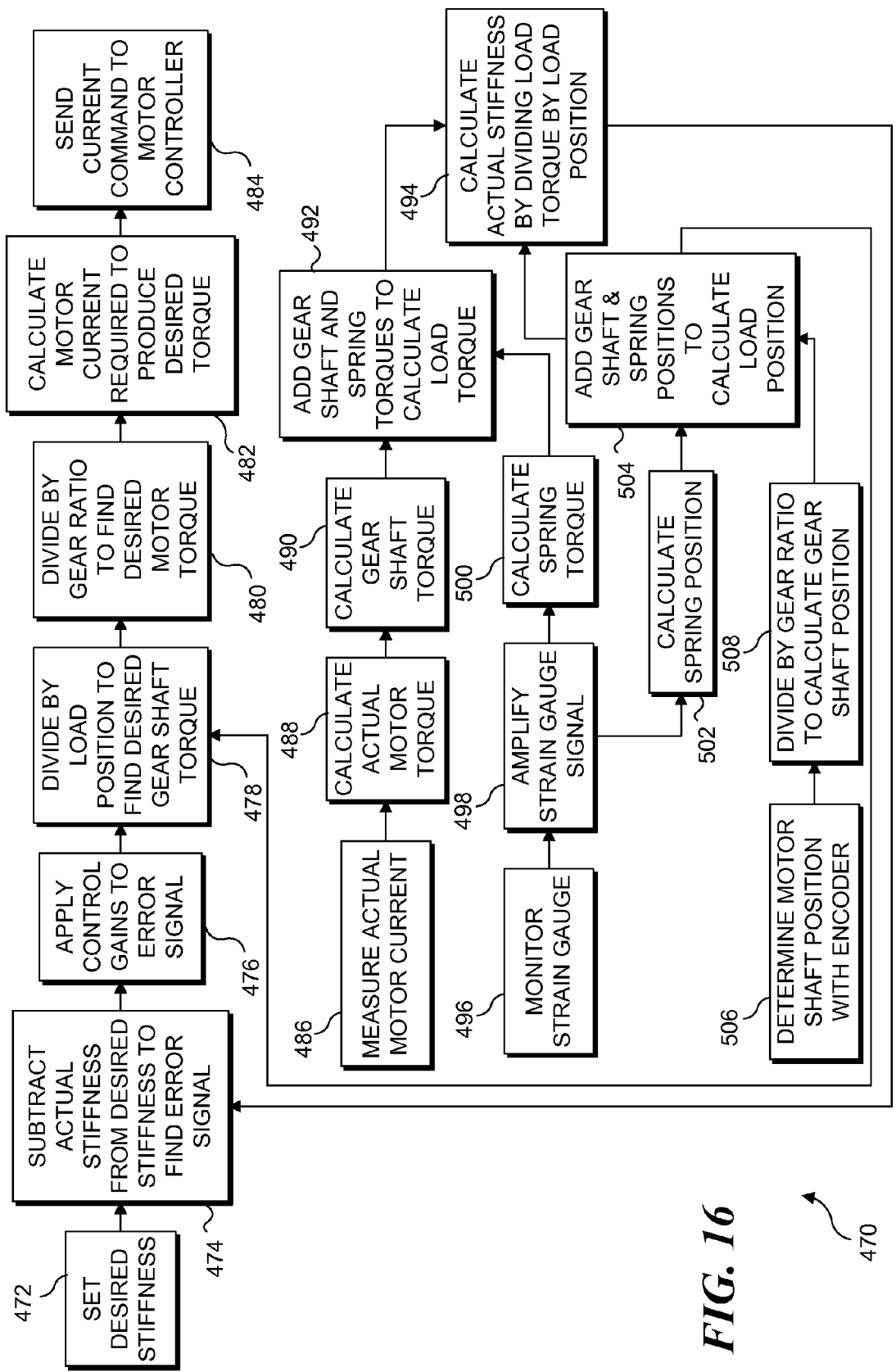
Figure 17:
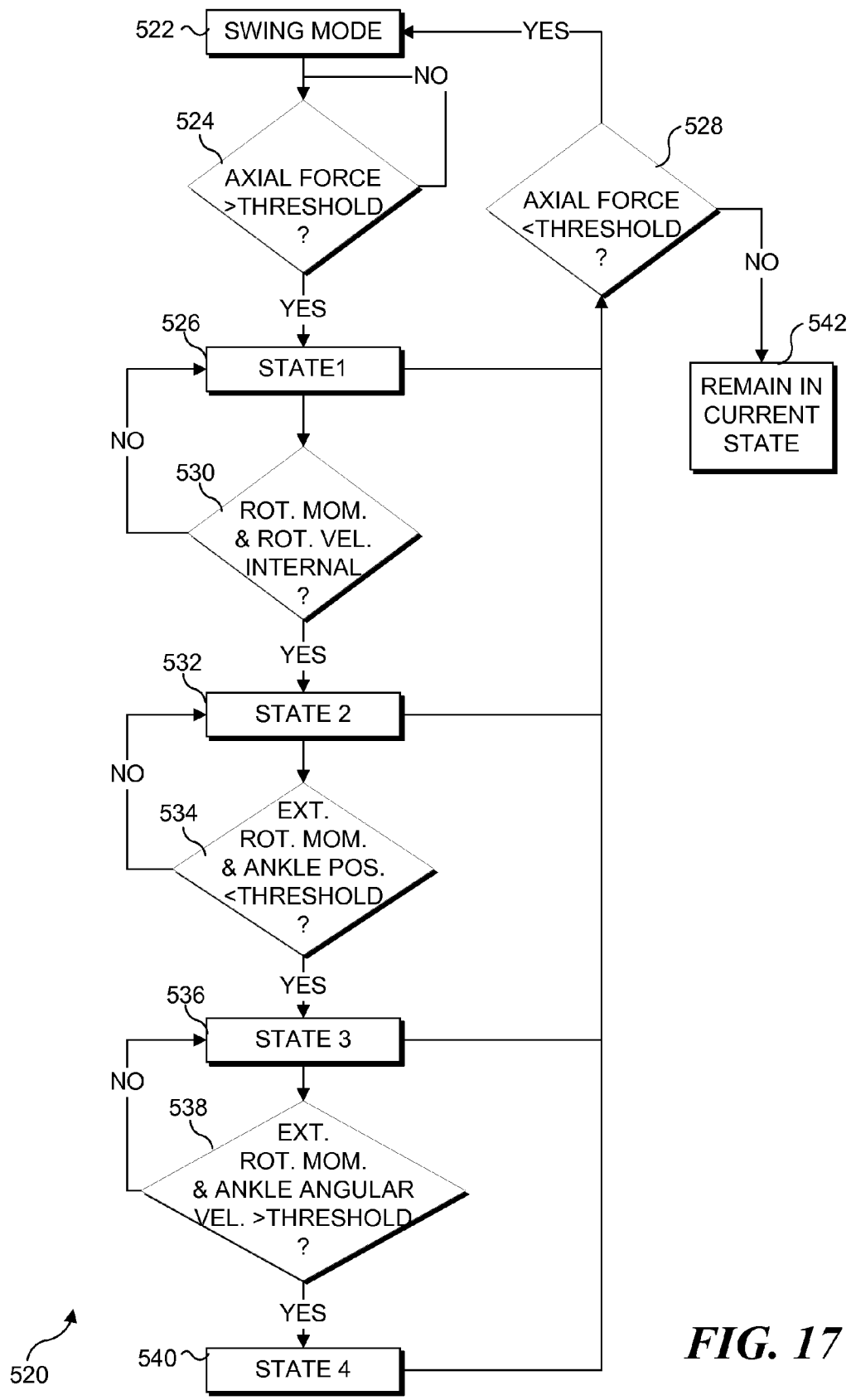
Figure 18:
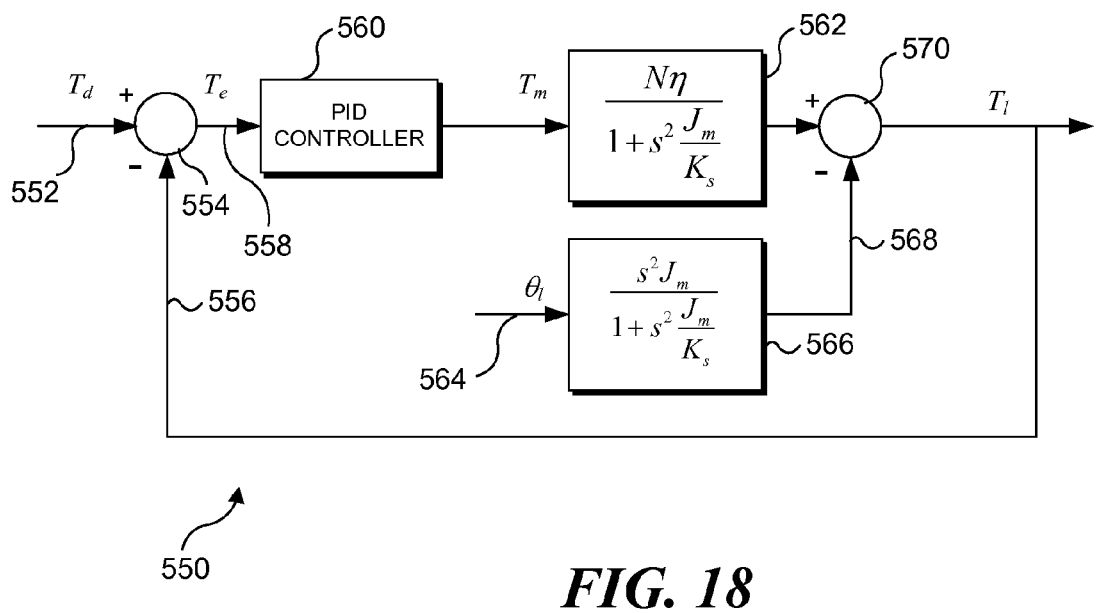

FIG. 3 includes four graphs respectively illustrating from top to bottom, ankle angle, ankle velocity, ankle moment, and ankle power, for each of four different states, where the data were captured for ten subjects who were walking ahead in a straight line;

FIG. 4 includes 12 graphs respectively illustrating the same parameters as in FIG. 3, for a 90 degree hallway turn, for the turn initiation, its apex, and its termination steps, again for data collected in regard to ten subjects;

FIG. 5 is a schematic image of a cruciform hinge used for a torsional spring employed in an exemplary TRA in accord with the present novel approach;

FIG. 6 is a schematic diagram of an impedance control system to control the effective stiffness in the exemplary TRA;

FIG. 7 is a schematic block diagram illustrating the four types of steps, including straight, turn initiation, turn apex, and turn termination, which might be intended by a person using a prosthesis incorporating the TRA of the present novel approach;

FIG. 8 is a flowchart of the logic employed by an exemplary finite state control system for implementing torque control during straight steps;

FIG. 9 is a flowchart of the logic employed by an exemplary finite state control system for implementing torque control during initiation steps;

FIG. 10 is a flowchart of the logic employed by an exemplary finite state control system for implementing torque control during apex steps;

FIG. 11 is a flowchart of the logic employed by an exemplary finite state control system for implementing torque control during termination steps;

FIG. 12 is an exploded view of an exemplary harmonic drive device that can be used for the gear reduction portion of the TRA in the present novel approach;

FIG. 13 is an exemplary functional block diagram of the TRA system;

FIG. 14 is an exemplary functional block diagram of a computing device suitable for use in the controller of the TRA in accord with the present novel approach;

FIG. 15 is a schematic side view of an exemplary prosthesis that includes the TRA in accord with the present novel approach;

FIG. 16 is a flowchart showing exemplary logical steps for controlling the TRA to achieve a desired stiffness in resisting the transverse rotational torque acting on a prosthesis;

FIG. 17 is a flowchart of the logic employed by an exemplary finite state control system for implementing torque control when attempting to achieve a desired torque for the TRA in an alternative exemplary embodiment; and FIG. 18 is a schematic block diagram of an exemplary torque control system for torque control mode used in the alternative embodiment.

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein. Further, it should be understood that any feature of one embodiment disclosed herein can be combined with one or more features of any other embodiment that is disclosed, unless otherwise indicated.

Preliminary Studies

To evaluate the hypothesis that turning is a requirement of activities of daily living, a study was performed using video data of the steps taken during several common activities. An investigator filmed the walking patterns of ten subjects below the waist while they performed the activities of walking from an office to a car, walking between two offices, purchasing goods at a convenience store, and purchasing a meal at a cafeteria. The study found that turning steps comprised up to 50% of the steps taken during a daily activity, that activities with more task demands like picking out items in a store or filling a drink cup at a cafeteria required more turning, and that shorter activities require more turning steps. Given these data and the fact that periods of walking by amputees tend to be of short duration, it can be concluded that turning is an important consideration for prosthetic design.

In a second study, the biomechanical strategies used to perform transient turning maneuvers were investigated. Ten subjects were asked to walk straight ahead and navigate a 90 degree hallway corner while force plates recorded kinetic data and a 12 camera Vicon™ system recorded motion data. First, a data processing method was developed to express the ground reaction impulses (GRIs) during a transient turn in terms of a body frame, rather than a global reference frame. The body frame had an origin at the body center of mass (COM) and was aligned to the COM trajectory. Then, the GRIs for straight walking and turning were compared. It was found that the braking and propulsive GRIs during the initiation and termination steps of the turn resembled the GRIs for decelerating and accelerating during straight walking, suggesting that the body modulates these impulses to control walking speed during a turn. The medial-lateral impulses acted in the direction away from the turn.

To determine the simplest system of mechanical elements that could mimic the intact human ankle, a mechanical model of the ankle in the transverse plane was created. First, the model investigated ankle behavior during straight walking. Motion capture data were collected of ten subjects walking straight ahead. The model divided the kinematic and kinetic data from the stance phase into four states, as shown in graphs 40 in FIG. 3, based on zero values in the power curve and investigated the elastic and viscous behavior of the ankle in each state. Viscous behavior was found to be negligible, and in the first state, the elastic behavior was found to resemble that of a quadratic torsional spring, while the remaining three states were found to resemble linear torsional springs.

Next, the model was used to investigate the simplest system of mechanical elements that could mimic the ankle in the transverse plane during turning.

Motion capture data were collected from ten subjects performing 90 degree hallway turns. As illustrated in graphs 50 in FIG. 4, data from turn initiation 52, apex 54, and termination 56 steps were investigated. States were separated for the kinematic and kinetic data, and elastic and viscous behaviors were investigated, yielding the graphical results shown in the graphs of rows 58, 60, 62, and 64 for each of the three types of steps 52, 54, and 56. It was found that, in general, the ankle softens during initiation steps, stiffens to maintain constant position during apex steps, and stiffens during termination steps.

Finally, as shown in FIG. 2, a dynamic actuator model was created to help determine the stiffness of a spring 38 for a series elastic actuator (SEA) 30 that would minimize power consumption while maximizing spring power amplification. The model was based on specifications for an RE-40™ brushless DC motor 32 (such as available from Maxon Precision Motors, Fall River, Mass.) that is coupled via a drive shaft 34 to a 353:1 GP52C™ gear reduction box 36 (also available from Maxon Precision Motors), the inertial characteristics of an 80 kg man, and kinetic and kinematic data for ten subjects walking straight ahead at self-selected speeds. Based on the results of the model, a stiffness of 250 N-m/rad was chosen. As shown in a model 70 in FIG. 5, a cruciform hinge geometry 72 was chosen for the torsion spring, and it was fabricated from titanium in an initial exemplary embodiment.

Design of the Impedance Control System

While the stiffness of the elastic element will not change, through an impedance control strategy, the effective stiffness, or the relationship between motor position and spring torque, can be controlled by dynamically varying the motor position with respect to the load position. Based on the dynamic actuator model, an exemplary control system 80, which is shown in FIG. 6, was developed.

As shown in FIG. 6, an input 82 to the proposed control system is the desired effective stiffness, $k_d$. This desired effective stiffness can be input by the user of the TRA or can be automatically determined based on a sensor that detects the type of activity or a parameter such as a slippage of the residual limb in the socket of the prosthesis or a sensor of some other parameter that is beneficial in controlling the stiffness of the TRA. An actual effective stiffness 86 of the TRA, $k_l$, is subtracted from $k_d$ in a summing junction 84 to find a stiffness error 88, $k_e$, which is passed to a proportional-integral-derivative (PID) controller 90. The error $k_e$ is multiplied in a multiplier 92 by an angular load position $\theta_l$, to find a motor torque, $T_m$. Transfer functions 94 and 98 respectively produce outputs 102 and 100 that are summed at a summing junction 104 to determine a load torque, $T_l$. An input 96, $\theta_l$ is supplied to transfer function 98. Transfer functions 94 and 98 employ the gear ratio N, gear box efficiency η, a constant, $K_s$, and polar moment of inertia $J_m$. An operation 106 using the reciprocal of $\theta_l$ is applied to $T_l$ to obtain actual effective stiffness 86.

Design of an Exemplary Finite State Control System

Human ankle behavior in the transverse plane can be described as a variable stiffness spring that varies its stiffness throughout the gait cycle, with periods differentiated by separate states in the stance phase (FIGS. 3-4). As such, a higher-level finite state control system is needed to switch between stiffness levels. Finite state control systems have been used in many prosthetic and orthotic systems, since the gait cycle is easily divisible into states.

To achieve a long term goal of providing a neurally-controlled prosthesis, some sort of upper level control system will be required to determine an intended step type 112, as shown in a block diagram 110 in FIG. 7. Each step type, straight 114, turn initiation 116, turn apex 118, and turn termination 120, will have its own corresponding finite state control system based on the states (FIGS. 8-11) determined from a biomechanical model of the step type. In the finite state diagrams, the control system will remain in a previous state until one of the anticipated conditions is met. For example, as shown in a flow chart 130 for the straight step type, in FIG. 8, the control system will remain in an S-State 1, as indicated in a block 138, until either the axial force falls below a defined threshold, or the rotator moment and velocity both enter the internal range. The details of this logic are explained below.

The flowchart in FIG. 8 begins at an upper loop 132 for a straight step 134. A decision step 136 determines if the axial force is greater than a threshold (indicating that the prosthetic foot is applying force against the ground or other adjacent surface), and if so, in a step 138, the control system changes to (or remains in) an S-State 1. If not, the logic loops until an affirmative result is returned. After entering S-State 1, a decision step 142 determines if both the rotator moment and rotator velocity are in the internal range, and if so, in a step 144, the control system changes to an S-State 2. If not, the logic remains in S-State 1 at step 138. While in step 138, the logic also periodically determines if the axial force is below the threshold, in a decision step 140. If the axial force becomes less than the threshold, as determined in decision step 140, the prosthesis is apparently swinging and not in contact with the ground or other adjacent surface. If not, the control system remains in the current state, as indicated in a step 154, but if so, the logic return to the upper loop in step 132. The logic repeatedly checks the conditions of decision steps 140 and 142 until a positive result is achieved to either decision step.

After entering S-State 2, the control system remains in that state until the condition in decision step 140 is met, or until both the rotator moment enters the external range and the ankle angular position is below a threshold value, as determined in a decision step 146. If both of these conditions occur, the control system enters the S-State 3, as indicated in a step 148. If either condition is not met, the logic remains in S-State 2 and periodically checks to determine if the axial force is below the threshold in decision step 140. After entering S-State 3, a decision step 150 determines if both the rotator moment is in the external range and the ankle angular position is above the threshold. If so, the control system enters an S-State 4 in a step 152, but if not, the control system remains in S-State 3. While in S-State 4, the logic periodically runs decision step 140. The control system remains in S-State 4 until decision step 140 determines that the axial force is below the threshold.

A flowchart 160 for a turn initiation step 164 is illustrated in FIG. 9 and starts at an upper loop 162. A decision step 166 determines if the axial force has exceeded a threshold and if so changes to (or remains in) an I-State 1, as noted in a step 168. If not, the logic loops until the condition in decision step 166 is met. After entering I-State 1, the logic periodically executes a decision step 170 to determine if the axial force is below the threshold, indicating that the prosthesis is not in contact with the ground or other adjacent surface. If the condition of decision step 170 is met, the logic returns to upper loop 162, but if not, the control system remains in the current state in a step 184. After entering I-State 1, the logic periodically also checks to determine if both the rotator moment and rotator velocity are in the internal range, as indicated in a decision step 172. If not, the control system remains in I-State 1. If these two conditions are met, the control system enters an I-State 2, as noted in a step 174. After entering I-State 2, the logic periodically executes decision step 170, which makes the determination discussed above. Also after entering I-State 2, if the condition of decision step 170 is not met, the control system remains in I-State 2 until the rotator moment enters the external range and the ankle angular position is below a threshold, as indicated in a decision step 176. If so, the control system enters I-State 3 in a step 178. If both of these conditions are not met, the logic remains in I-State 2, and periodically checks to determine if the axial force is below the threshold in decision step 170 or if the conditions of decision step 176 are met. After the control system enters I-State 3, the control system periodically determines if the condition of decision step 170 is met, and if the rotator moment has entered the external range, and the ankle angular position is above the threshold, in a decision step 180. If not, then the control system remains in I-State 3. But, if the conditions of decision step 180 are met, the control system enters I-State 4 in a step 182. Again, the logic periodically makes the determination in decision step 170, as discussed above.

The turn apex is illustrated at a step 194 in a flowchart 190 that is shown in FIG. 10. The turn apex begin at an upper loop in a step 192. A decision step 196 determines if the axial force is exceeding a threshold, indicating that the prosthesis is in contact with the ground or other adjacent surface. The logic loops until this condition is met. Once the threshold is exceeded, the control system enters (or remains) in an A-State 1 in a step 198. After entering A-State 1, the logic periodically runs a decision step 200 to determine if the axial force is below the threshold and if so, returns to the upper loop. If not, the logic remains in the current state, in a step 206. Also, after entering A-State 1, a decision step 202 determines if the rotator moment has entered the external range, and if not, simply remains in A-State 1. If so, the control system enters an A-State 2 in a step 204. The logic remains in A-State 2, until upon a periodic check in decision step 200, the axial force is found to be less than the threshold, which resets the logic to the upper loop in step 192.

Finally, for a turn termination in a step 214, a flowchart 210 shown in FIG. 11, starts at an upper loop in a step 212. A decision step 216 determines if the axial force exceeds the threshold, and if not, simply loops until it does. Once the axial force is greater than the threshold in decision step 216, the control system enters a T-State 1 in a step 218. After entering T-State 1, the logic periodically checks to determine if the axial force has dropped below the threshold in a decision step 220. If so, the logic returns to upper loop 212, but if not, the control system remains in the current state in a step 230. Periodically, the logic determines if the rotator moment is in the external range and the ankle position is below a threshold, in a decision step 222. If not, the control system remains in T-State 1. But if so, the control system enters a T-State 2 in a step 224. Once T-State 2 is achieved, the logic again periodically checks the axial force in decision step 220, and also periodically determines if the external rotator moment has entered the external range and if the ankle position is above a threshold in a decision step 226. Until both conditions are met, the control system remains in T-State 2. But once both of these conditions are met, the control system enters a T-State 3 in a step 228. The control system remains in T-State 3 until the axial force is less than the threshold in decision step 220.

Ambulating in the real-world environment is a highly uncertain task. Limiting the control system to an already occupied state until specific criteria are met can allow amputees to adjust steps with a predictable stiffness. For example, an amputee might start a turn initiation step, only to observe another person has stepped into the intended trajectory, forcing the amputee to react with kinematic and kinetic patterns that differ from the initiation steps. In this case, the control system should remain in I-State 1 to give the amputee predictable prosthesis behavior in order to complete the step before the control system resets itself during the swing phase and gets ready for the next step.

A strain gauge on the prosthesis can be used to detect axial loading to determine if the prosthesis is in a stance phase (exerting a force on the ground or other adjacent surface), or in a swing phase. A separate strain gauge is employed to sense torque in the elastic element of the SEA and is used in determining the moment used for state transitions. An optical encoder on the motor shaft can be used to determine the angular position and velocity data for state transitions.

Control System Simulation

As a preliminary validation of the control system design, simulation experiments were performed. Ankle torque and position data from previous experiments were used as $T_l$ and $\theta_l$, respectively. The value $k_d$ was provided from the ankle models developed previously. The effective actuator stiffness $k_a$, or the quotient of $T_{spring}$ and $\theta_{spring}$ are calculated throughout the gait cycle. The control elements can be tuned manually until $k_a$ matches $k_d$, within an error range of ±5%.

The performance of the control system with a physical actuator was confirmed through bench top testing. The actuator used in this initial exemplary prototype was based on the design from the previous work and included a cruciform hinge made of titanium, an RE-40™ brushless DC motor (Maxon) and a 353:1 GP52C™ gearbox (Maxon). The actuator was mounted in an MTS 858 Bionix™ system. Transverse plane ankle kinematics were simulated with the MTS's displacement control feature. The actuator was controlled in real time. Again, the control elements were tuned manually until $k_a$ matched $k_d$, within an error range of ±5%

Functional Block Diagram

FIG. 13 is a functional block diagram of an exemplary TRA system 410. A TRA 422 that is used in a prosthesis in place of a conventional pylon is controlled by a computing device (or other logic device) 416. The logic device can be either hard-wired or can be a microcontroller or an application specific integrated circuit (ASIC). Power for energizing a motor 424, computing device 416, and other components of the system is supplied by a power supply 412, which includes a battery or other portable power source. A motor controller 414 is controlled by the computing/logic device to vary the current supplied to motor 424. A current sensor 418 monitors the current being supplied to motor 424, producing a current indicative signal that is supplied to a data acquisition circuit 420. This analog signal can be converted to a digital signal by the data acquisition circuit, for input to computing/logic device 416. An encoder 426 (e.g., an optical encoder) monitors the motor shaft position, producing a position signal that is input to motor controller 414, to aid in controlling the current supplied to motor 424 to achieve a desired stiffness of the prosthesis (or in an alternative exemplary embodiment, a desired torque).

Since the motor shaft turns at a relatively high speed compared to the driven torque applied by the TRA, a gear reduction module 428 is included to couple the motor to a torsional spring 430. Attached to torsional spring 430 are a pair of strain gauges 432, which produce strain indicative signals (one axial and one torsional) that are input to an amplifier 434. The amplified strain signals are then input to data acquisition circuit 420, for input as digital strain signals to computing device 416. The user can manually adjust a set point dial 436 to vary the stiffness of the TRA (or a range of stiffness), as desired for specific activities in which the user wants to participate, as explained above. Accordingly, it is intended that the stiffness or torque resistance provided by the TRA might also be automatically and dynamically modified within a range set by the user using the set point dial or other user-manual control for input. It should be noted that instead of a dial (which might control a variable potentiometer), the desired stiffness or range of stiffness (or desired torque or range of torque) may instead be set by the user by an input to a digi-switch, a joystick, or other input device for a user-variable setting of a parameter.

FIG. 14 illustrates further details of an exemplary computing device 416 (or other logic device), which is suitable for controlling the TRA as discussed herein. This exemplary computing device includes a processor 440, which executes machine readable and executable software instructions that are stored in a memory 442. Processor 440 receives input signals, such as from data acquisition circuit 420 or from set point dial 436 via input/output (I/O) ports 444. The processor executes the machine software instructions to produce output signals that are supplied to motor controller 414 through the I/O ports. These software instructions cause the processor to execute the control functions indicated in the flowchart of FIG. 16, as noted below. Similar control functions are implemented when the alternative exemplary embodiment is employed to achieve a desired torque with the TRA.

Embodiment Appropriate for Prosthesis

The experimental actuator and control system will be incorporated into a prosthesis. For this step, a new actuator, with smaller, lighter components more suitable for a prosthesis is being designed, and a mechanical interface is being developed to incorporate the actuator into a transtibial prosthesis. It should be understood that the general approach embodied in the exemplary embodiments disclosed herein are equally applicable to prosthetic devices for other portions of a patient's body and are not limited only to a transtibial prosthesis.

When designing lightweight actuators, the limiting factor is often not the maximum motor torque, but instead, the maximum permissible torque for a particular planetary gear transmission system. To achieve biomimetic torques while maintaining an appropriate safety factor, the gearbox chosen in the initial exemplary prototype had a mass of 770 grams, which is far too great for a prosthesis.

Fortunately, other types of transmission systems are available. One particularly promising technology is called a Harmonic Drive, an exploded isometric view 230 of which is illustrated in FIG. 12. In a Harmonic Drive, the motor shaft is drivingly coupled to an elliptical disc called a Wave Generator 236. The Wave Generator is inserted into a thin-walled cup called a Flexspline 234. The Flexspline has gear teeth machined into the outer edge and conforms to the Wave Generator's elliptical shape. The Flexspline acts as the output of the transmission and is inserted into a Circular Spline 232. The Circular Spline is a rigid steel ring with internal gear teeth and is attached to the transmission housing and does not rotate. The teeth of the Flexspline interact with the teeth of the Circular Spline along the longitudinal axis of the Flexspline. And, since the Flexspline has fewer teeth than the Circular Spline, with every revolution of the Wave Generator, the Flexspline shifts relative to the Circular Spline as a function of the difference in the number of teeth on the two splines, creating an effective gear reduction as the Flexspline rotates slowly in the opposite direction from the Wave Generator. The main benefit of this technology is that high gear ratios can be achieved in compact, lightweight devices. It is noted that this technology could alternatively use a planetary gearbox (such as those made by Maxon Motors of Sachsein, Switzerland), or a spur gearbox (such as those made by Maxon), an Ikona Gear Drive (such as those made by Ikona, Port Coquitlam, Canada), or other types of gear (speed) reduction transmissions or mechanisms.

In a more lightweight and compact embodiment for a prosthesis, a CSF-14™ Harmonic Drive Mini Gearhead (available from Harmonic Drive, Hauppauge, N.Y.) can be used. This particular model has a 100:1 gear ratio, can achieve peak torques of 28 N-m, and is only 295 grams in mass. The use of this Harmonic Drive should also enable a smaller motor to be used for the TRP than the one used in the initial exemplary prototype. For example, in this new embodiment, a RE-30™ (Maxon) motor, which has a mass of 238 g, can be employed, providing a savings of over 242 g compared to the motor used in the prototype. The Maxon RE-40™ motor used in the initial prototype has a nominal voltage of 24 VDC, a maximum continuous torque of 170 N-mm, and a stall torque of 2280 N-mm. In contrast, the Maxon RE-30™ motor that may be used in the TRA sized to fit in a prosthesis has a nominal voltage of 12 VDC, a maximum continuous torque of 51.7 N-mm, and a stall torque of 844 N-mm. It is likely that future embodiments of the novel TRA will be achieved that include even smaller (and perhaps more powerful motors), so long as a gear reduction mechanism with a suitable gear ratio/weight ratio, and load capability is employed.

In the initial prototype, the elastic element stiffness of the experimental actuator was chosen based on simulations investigating motor power consumption and spring power amplification. For the new light and compact embodiment that will be appropriate for use in a prosthesis, a stiffness value for the prosthetic actuator can be selected based on both motor power consumption and spring power amplification. Additionally, the effect of stiffness values on control system stability can be empirically determined by measuring settling time through simulations.

Similar to the initial prototype, a dynamic actuator model will be constructed using similar components to those described above in the prototype. Gait simulations will be performed with the actuator model to determine the effect of differing stiffness values on motor power consumption and spring power amplification. Then, using the control system that is designed, the effect of differing stiffness values on control system stability will be investigated. A stiffness value for the prosthetic actuator will be chosen qualitatively based on these three investigations.

An elastic element for the new actuator can be made with the Alibre Design™ (Alibre, Richardson, Tex.) solid modeling software. A cruciform hinge geometry will likely be chosen again, for its resistance to compressive and bending loads and for its ability to deform torsionally. The elastic element will be fabricated from titanium for its high shear modulus-to-yield-strength ratio. The proximal end of the element can be designed to interface with the harmonic drive, while the distal end can be designed to interface with a standard female prosthetic pyramid adaptor.

A housing can be designed to connect the TRA to a prosthetic socket. For example, the housing can also be created with the Alibre Design™ tool (Alibre) and can connect the Harmonic Drive to the socket in such a way that the motor is never loaded axially.

FIG. 15 illustrates further details of this embodiment, showing an example of how it will be integrated into a prosthesis. TRA 410 extends between a socket 458 in which an amputee's residual limb (not shown) is inserted. Socket 458 is coupled to the TRA by brackets 454 (or sides or a housing), which extend downwardly from each side of the socket and are coupled to gear reduction mechanism 428 immediately above a proximal end 446 of torsion spring 430. The components that control the TRA are miniaturized and are generally disposed within a controller 456 that is disposed immediately below the socket, although other convenient locations can instead be used. Details of the power supply are not shown in this view, but a battery pack 462 is shown attached to one side of brackets 454. It will be appreciated that additional battery packs can be attached to the other sides of the brackets, or that the battery pack(s) can instead be disposed at other locations on the prosthesis, e.g., within an artificial foot 452.

Artificial foot 452 is coupled to a distal (lower) end 448 of torsion spring 430 and is secured by a clamp 450. Other components of the TRA are identified by the reference numbers listed above. A user accessible knob 460 is provided to enable a user to adjust the desired stiffness (or range) or desired torque (or range) provided by TRA 410 and is coupled to set point dial 436 by an input shaft (not indicated).

Flow Chart Illustrating Exemplary Steps of Control Logic

FIG. 16 illustrates exemplary steps 470 that can be implemented by the computing device or other logic device to control the operation of the TRA to achieve a desired stiffness. In a step 472, the user can input or set the desired stiffness (or range of stiffness) for the TRA. The actual desired stiffness can be determined from the models discussed above, to correspond to that experienced by the limb of an intact person when ambulating. By setting the range of the desired stiffness, the user can shift the peaks of the modeled parameters as desired. Alternatively, the desired stiffness can be determined only from such models without any input from the user.

A step 474 then subtracts the actual stiffness from the desired stiffness to determine an error signal. Control gains (i.e., amplification) are applied to the error signal in a step 476. In a step 478, the amplified error signal is divided by a load position (determined as explained below) to determine a desired gear shaft torque that should be applied by the electric motor of the TRA. This desired gear shaft torque is divided by a gear ratio of the gear reduction transmission to determine a desired motor torque, in a step 480. The motor electrical current that is required to produce the desired motor torque is calculated in a step 482. The magnitude of the electrical current is supplied as a current command to the motor controller in a step 484, which then provide electrical current at that magnitude to energize the electric motor used as a prime mover.

Returning back to step 474, the actual stiffness must be determined by data calculated using two parallel logic paths. The first of these logic paths starts with a step 486, which measures the actual electrical motor current being applied to drive the electrical motor. Based on this electrical current, a step 488 calculates the actual motor torque that is being produced by the motor. Using this actual motor torque, a step 490 calculates the gear shaft torque. In a step 492, the gear shaft and spring torques are added to determine the load torque being applied. This value for load torque is supplied to a step 494.

The second logic path begins with a step 496, which monitors the strain gauge mounted to the elastomeric torsion spring. The signal produced by the strain gauge is amplified in a step 498, and in a step 500, the amplified strain gauge signal is used to calculate the spring torque. The spring torque is supplied to step 492 for use in calculating the load torque. Also, the amplified strain gauge signal is used in a step 502 to calculate the torsion spring position. A step 506 determines the motor shaft position using an encoder, and a step 508 divides the motor shaft position by the gear ratio to determine the gear shaft position. A step 504 then adds the gear shaft and torsion spring positions to calculate the load position. The load position is then supplied to step 494, and also to step 478, for use as discussed above. Step 494 calculates the actual stiffness of the prosthesis (at the present time) by dividing the load torque by the load position. The resulting actual stiffness is provided to step 474, for use as noted above. In the alternative embodiment of the TRA discussed below that controls load torque rather than stiffness, the desired load torque of the prosthesis can be compared to the actual load torque (instead of comparing the desired stiffness to the actual stiffness). It should be evident how to modify FIG. 16 to achieve load torque control rather than stiffness control.

Torque Control Embodiment

As noted in the background and significance section, lower limb amputees expend much more metabolic energy while walking than intact individuals. Research has shown that amputees are unable to effectively generate the simultaneous positive and negative work with the trailing and leading limbs required to redirect the COM to new pendular trajectories due to the passive nature of most prosthetic components. This result suggests that powered components could reduce the metabolic cost of walking and indeed, preliminary work with a powered sagittal ankle prosthesis has demonstrated a 14% decrease in metabolic cost in three transtibial amputees. However, substantial energy is also required to redirect the COM in the frontal plane. It is expected that active power generation in the transverse plane can help redirect the COM towards the contralateral limb and thus reduce the metabolic cost of this movement.

Active transverse ankle torque generation is believed to influence step-to-step transitions and consequently, should reduce the metabolic cost of walking for lower limb amputees. In an alternative exemplary embodiment of the present novel TRA, a new control mode is used with the TRA to actively generate a desired torque, rather than controlling the TRA to achieve a desired stiffness. This alternative approach employs a state-based torque control system. State-based control systems are useful for prosthetic limb applications because they can enable the prosthesis to perform different functions in different parts of the gait cycle. The Rheo Knee™, which is produced by Ossur of Aliso Viejo, Calif., uses a state-based controller to adjust sagittal-plane mechanical resistance as needed throughout the stance and the swing phase of walking Similarly, the PowerFoot One™, available from iWalk™, of Cambridge, Mass., uses a state-based system to adjust mechanical resistance in early and mid-stance phase and then, actively generates torque in the sagittal plane in the late stance. However, for the TRA, a state-based system is employed to govern mechanical resistance and torque generation in the transverse plane of the prosthesis.

It should be noted that if desired, a user may be provided a control to switch the TRA control system to either achieve a desired stiffness (which will typically provide enhanced comfort to the user), or a desired torque (which will typically reduce the metabolic load on the user—but may not be as comfortable). It is also contemplated that the selection of controlling the TRA to achieve a desired stiffness or a desired torque may be achieved automatically as the user of the prosthesis with the TRA engages in different types of activity, since the choice of the controlling parameter—i.e., either stiffness or torque, can automatically be optimized based on the type of activity in which the user is participating. For example, if the user is participating in a sports activity, the rapid changes in the parameters such as axial load and rotational movement can indicate that the user would be best served by employing the torque control embodiment rather than the stiffness control embodiment. Conversely, if the user is simply walking down the street, or engaging in less vigorous movements, the control system can automatically detect the lower level of activity and rotation movement to select the control based on stiffness.

In this exemplary embodiment for controlling torque, an upper level state-based control system determines the stage of a gait cycle of the prosthesis at a given time and then, instructs a lower level impedance or torque control system to behave accordingly. States are determined based on information from local sensors on the active TRA, as shown for a flowchart 520, in FIG. 17, and generally as discussed in connection with the first exemplary embodiment intended to achieve a desired stiffness. The flowchart start with a swing mode in a step 522. When the load on the series elastic element is below a threshold of 20 N, for example, the system assumes that the active TRA is in the swing mode and sets itself in a neutral position in preparation for a heel strike, which is detected by monitoring the axial force. The logic repeatedly checks in a decision step 524 to determine if the axial force is greater than a threshold, and if not, remains in the swing mode. Once the axial force threshold is exceeded, as the heel of the prosthesis contacts the ground or other adjacent surface, the system switches to a State 1 in a step 526 and uses the impedance control system from the first exemplary embodiment (based on achieving a desired rotational stiffness of the TRA) in a decision step 530 to determine if the rotator moment and rotator velocity have entered the internal range. If so, the state system changes to a State 2 in a step 532, and the stiffness input changes to the appropriate value for this state. Periodically, when in State 1 or State 2, the control system determines if the axial force is less than the threshold in a decision step 528. If not, the control system remains in the current state, in a step 542. However, if the axial force becomes less than the threshold in decision step 528, then the control system returns to the swing mode at step 522. After switching to State 2, in step 532, a decision step 534 is periodically executed to determine if the rotator moment has entered the external range and if the ankle angular position is less than a threshold. If so, the system control switches into a State 3 at a step 536. The lower level torque controller (see below) is employed to provide a torque burst to the system. Periodically, while in State 3, the logic executes decision step

528 determines if the axial force has become less than the threshold, as discussed above. Also, a decision step 538 periodically determines if the rotator moment is in the external range and if the ankle angular velocity is greater than a threshold (for example, 20 deg/sec). If not, the control system remains in State 3, but if both conditions in decision step 538 are met, then the control system switches to State 4 at a step 540, supplying the appropriate torque trajectory to the torque control system. The control system remains in State 4 until the axial force slips below the threshold, as determined in decision step 528, and the control system then again returns to the swing mode.

The torque controller, which is shown in a schematic diagram 550 in FIG. 18, works as follows. A desired torque 552, which is represented by $T_d$, is input to the control system and the difference between this desired torque and an actual load torque 556, which is indicated by $T_l$, is determined by a summing junction 554, yielding a torque error 558. The torque error, $T_e$, is then passed to a PID controller 560. The PID controller produces a motor torque input, $T_m$, which is applied to transfer functions 562 and 566 relating the load torque $T_l$ to $T_m$ and $\theta_l$. The load angle $\theta_l$ is provided on an input 564. The transfer functions include the gear ratio, N, gear box efficiency, $\eta$, and polar moment of inertia, $J_m$, as well as a constant, $K_s$. (In the equations for the transfer functions, s is a state variable applied when using a Laplace transform to change from the time to the frequency domain.) An output 568 of transfer function 566 is subtracted from the output of transfer function 562 at a summing junction 570, yielding the value for $T_l$, which is provided to summing junction 554, as noted above and is also used to control the current produce by the prime mover (i.e., the electric motor in this exemplary embodiment).

Neural Interface

It is contemplated that future generations of the novel TRA may utilize a neural input to set the desired stiffness level in the impedance control system. In such an embodiment, a high level control system will determine the type of step (straight, turn initiation, stair descent, etc.) that the amputee is performing or intends to perform, and an intermediate level control system will determine the state of the step in which the prosthesis is and look up the appropriate stiffness for that state in a look-up table. Also, a lower level impedance control system will then use that stiffness as a set-point to control the actual stiffness of the TRA in the prosthesis.

Several different types of neural inputs may be used in future generations of the present novel TRA to provide the desired torque or the desired stiffness instead of a direct user input or simply using the values derived from the model of steps by an intact individual. Without intending any limitation, examples of such neural inputs include surface electromyogram (EMG) electrodes (such as those made by Noraxon, in Scottsdale, Ariz.), which are placed on the skin of the residual limb or other areas of the amputee's body; implantable EMG sensors (such as the BIONS™ being developed by the Alfred E. Mann Foundation at the University of Southern California, Los Angeles, Calif.), which are injected into the muscle tissue, longitudinal intrafascicular electrodes (such as those being developed at the Department of Bioengineering at the University of Utah, Salt Lake City, Utah), which screw into peripheral nerves, and other types of neural interfaces.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A transverse rotation adaptor for use with a prosthesis, to dynamically enhance performance of the prosthesis by controlling a rotational characteristic of the prosthesis in a transverse plane, comprising:
   a prime mover provides a rotational force that modifies the rotational characteristic of the prosthesis, the prime mover providing a first portion of a desired modification of the rotational characteristic;
   a speed reduction mechanism that is coupled with a drive shaft of the prime mover, to reduce a rotational speed of the drive shaft at an output of the speed reduction mechanism;
   an elastomeric component that is coupled with the output of the speed reduction mechanism and which is configured to couple with a member of a prosthesis that contacts a surface against which a rotational torque is developed, the elastomeric component providing a second portion of the desired modification of the rotational characteristic;
   at least one sensor that produces a signal indicative of at least one parameter used for controlling the transverse rotation adaptor when controlling the rotational characteristic; and
   a controller for automatically controlling the prime mover in response to the signal, to achieve the desired modification of the rotational characteristic of the prosthesis.

2. The transverse rotation adaptor of claim 1, wherein the desired modification comprises a modification of one of:
   (a) a stiffness provided by the transverse rotational adaptor during rotation; and
   (b) a torque provided by the transverse rotational adaptor during rotation.

3. The transverse rotation adaptor of claim 1, wherein the at least one sensor comprises at least one of:
   (a) a strain sensor that is coupled to the elastomeric component to monitor a strain in the elastomeric component to determine a torque provided by the elastomeric component;
   (b) a sensor that detects a magnitude of an axial load experienced by the prosthesis when contacting an adjacent surface; and
   (c) an angular sensor to determine an angular position of at least one portion of the transverse rotation adaptor.

4. The transverse rotation adaptor of claim 1, wherein the elastomeric component comprises a torsion spring.

5. The transverse rotation adaptor of claim 1, further comprising a user input device for enabling a user to selectively set or adjust the desired modification of the rotational characteristic for the transverse rotation adaptor.

6. The transverse rotation adaptor of claim 1, wherein the speed reduction mechanism comprises one of:
   (a) a harmonic drive;
   (b) a planetary gearbox;
   (c) a spur gearbox; and
   (d) a gear drive transmission.

7. A method for dynamically enhancing performance of a prosthesis by enabling control of a rotational characteristic of the prosthesis in a transverse plane, comprising the steps of:
   defining a desired modification of the rotational characteristic of the prosthesis during a transverse plane rotation;

energizing a prime mover to provide a portion of the desired modification of the rotational characteristic;

employing an elastomeric element in the prosthesis to provide a remaining portion of the desired modification of the rotational characteristic;

sensing one or more parameters for use in controlling the prime mover to achieve the desired modification of the rotational characteristic; and controlling the prime mover in response to the one or more parameters, so as to achieve the desired modification of the rotational characteristic provided the prosthesis during the transverse plane rotation.

8. The method of claim 7, wherein the step of defining the desired modification of the rotational characteristic comprises the step of enabling a user to selectively set the desired modification of the rotational characteristic in regard to either a specific level or a range of the desired modification.

9. The method of claim 7, wherein the step of defining the desired modification of the rotational characteristic comprises a modification of at least one of:
(a) a desired stiffness experienced by a user of the prosthesis during rotational movement; and
(b) a desired torque experienced by a user of the prosthesis during rotational movement.

10. The method of claim 7, wherein the step of sensing the one or more parameters comprises the step of sensing a strain in the elastomeric element that is indicative of a torque produced by the elastomeric element.

11. The method of claim 7, wherein the step of sensing the one or more parameters comprises the step of sensing a magnitude of an electrical current supplied to energize the prime mover, to enable a torque provided by the prime mover to be determined.

12. The method of claim 7, wherein the step of sensing the one or more parameters comprises the step of sensing an angular position of a part of the prosthesis.

13. The method of claim 7, wherein the step of sensing the one or more parameters comprises the step of sensing a magnitude of an axial load experienced by the prosthesis when contacting an adjacent surface.

14. The method of claim 7, wherein the step of controlling the prime mover comprises the step of determining an error corresponding to a difference between a desired stiffness and an actual stiffness of the prosthesis in resisting a rotational torque.

15. The method of claim 7, wherein the step of controlling the prime mover comprises the step of determining an error corresponding to a difference between a desired torque and an actual torque experienced by the user of the prosthesis during a rotational movement.

16. A method for dynamically enhancing performance of a prosthesis by enabling control of a rotational characteristic of the prosthesis during a transverse plane rotation, comprising the steps of:

defining a desired modification of the rotational characteristic of the prosthesis during a transverse plane rotation;

energizing a prime mover to provide a portion of the desired modification of the rotational characteristic;

employing an elastomeric element in the prosthesis to provide a remaining portion of the desired modification of the rotational characteristic;

sensing one or more parameters for use in controlling the prime mover to achieve the desired modification of the rotational characteristic;

controlling the prime mover in response to the one or more parameters by determining an error corresponding to a difference between a desired torque and an actual torque experienced by the user of the prosthesis during a rotational movement, so as to achieve the desired modification of the rotational characteristic provided the prosthesis during the transverse plane rotation; and wherein the step of controlling the prime mover further comprises the step of dividing the error by a position of a load applied to the prime mover to determine the desired torque to be produced by the prime mover.

17. A method for dynamically enhancing performance of a prosthesis by enabling control of a rotational characteristic of the prosthesis during a transverse plane rotation, comprising the steps of:

defining a desired modification of the rotational characteristic of the prosthesis during a transverse plane rotation;

energizing a prime mover to provide a portion of the desired modification of the rotational characteristic;

employing an elastomeric element in the prosthesis to provide a remaining portion of the desired modification of the rotational characteristic;

sensing one or more parameters for use in controlling the prime mover to achieve the desired modification of the rotational characteristic;

controlling the prime mover in response to the one or more parameters by determining an error corresponding to a difference between a desired stiffness and an actual stiffness of the prosthesis in resisting a rotational torque, so as to achieve the desired modification of the rotational characteristic provided the prosthesis during the transverse plane rotation; and wherein the actual stiffness of the prosthesis is determined by carrying out the steps of:
(a) calculating a shaft torque produced by the prime mover;
(b) calculating a spring torque produced by the elastomeric element;
(c) adding the shaft torque to the spring torque to determine a load torque applied to the prosthesis; and
(d) calculating the actual stiffness by dividing the load torque by a load position of the prosthesis.

18. The method of claim 17, further comprising the step of determining the load position by carrying out the steps of:
(a) calculating a position of the elastomeric element;
(b) calculating a shaft position for a shaft driven by the prime mover; and
(c) adding the position of the elastomeric element to the shaft position to determine the load position.

19. The method of claim 18, wherein the step of calculating the position of the elastomeric member comprises the step of monitoring a strain experienced by the elastomeric member during rotational movement.

20. The method of claim 18, wherein the step of calculating the shaft position comprises the steps of:
(a) monitoring a position of the prime mover; and
(b) dividing the position of the prime mover by a gear ratio of a speed reduction device that is driven by the prime mover, to determine the shaft position at an output of the speed reduction device.

21. The transverse rotation adaptor of claim 1, wherein the prosthesis is configured to extend from a residual limb along a prosthetic limb length and the transverse plane being transverse to the prosthetic limb length adjacent the residual limb.

22. The method of claim 7, wherein the prosthesis is configured to extend from a residual limb along a prosthetic limb length and the transverse plane being transverse to the prosthetic limb length adjacent the residual limb.

23. A transverse rotation adaptor for use with a prosthesis, to dynamically enhance performance of the prosthesis by controlling a transverse rotational characteristic of the prosthesis during a transverse plane rotation, comprising:
    a prime mover coupled with an elastomeric component, the prime mover configured to modify the transverse rotational characteristic of the prosthesis at least by adjusting an actual effective stiffness of the elastomeric component to a desired effective stiffness so as to provide a desired modification to the transverse rotational characteristic.

\* \* \* \* \*